(12) United States Patent
Yoshino et al.

(10) Patent No.: US 10,945,591 B2
(45) Date of Patent: Mar. 16, 2021

(54) IMAGE CAPTURING DEVICE, ENDOSCOPE APPARATUS, AND METHOD FOR OPERATING IMAGE CAPTURING DEVICE

(71) Applicant: OLYMPUS CORPORATION, Tokyo (JP)

(72) Inventors: Koichiro Yoshino, Tokyo (JP); Kanako Saito, Mitaka (JP)

(73) Assignee: OLYMPUS CORPORATION, Tokyo (JP)

( * ) Notice: Subject to any disclaimer, the term of this patent is extended or adjusted under 35 U.S.C. 154(b) by 418 days.

(21) Appl. No.: 15/964,461

(22) Filed: Apr. 27, 2018

(65) Prior Publication Data

US 2018/0242829 A1    Aug. 30, 2018

Related U.S. Application Data

(63) Continuation of application No. PCT/JP2015/080261, filed on Oct. 27, 2015.

(51) Int. Cl.
*A61B 1/045* (2006.01)
*H04N 5/232* (2006.01)
(Continued)

(52) U.S. Cl.
CPC .......... *A61B 1/045* (2013.01); *A61B 1/0002* (2013.01); *A61B 1/0005* (2013.01);
(Continued)

(58) Field of Classification Search
CPC . A61B 1/045; A61B 1/00105; A61B 1/00009; A61B 1/042; A61B 1/00126;
(Continued)

(56) References Cited

U.S. PATENT DOCUMENTS 9,645,473 B2 * 5/2017 Tsuruoka ........... A61B 1/00188
2004/0130651 A1 7/2004 Wakashiro
(Continued)

FOREIGN PATENT DOCUMENTS

JP   H02-304413 A   12/1990
JP   2001-013398 A   1/2001
(Continued)

OTHER PUBLICATIONS

International Search Report dated Jan. 26, 2016 issued in PCT/JP2015/080261.

*Primary Examiner* — Seung C Sohn
(74) *Attorney, Agent, or Firm* — Scully, Scott, Murphy & Presser, P.C.

(57) ABSTRACT

An image capturing device includes a processor. The processor is configured to implement: a switching control process for switching between a manual focus (MF) mode and an auto focus (AF) mode of performing auto focus control; a process for controlling driving of a focus lens; scene status determination process for performing a detection process for detecting a scene change during the MF mode and an estimation process for estimating distance change information indicating distance change between the image capturing section and an object. The processor is configured to implement: controlling the driving of the focus lens based on lens drive information; switching control for switching from the MF mode to the AF mode when the scene change is detected; and controlling the driving of the focus lens to bring the object into focus based on the distance change information.

20 Claims, 13 Drawing Sheets

(51) Int. Cl.
*A61B 1/00* (2006.01)
*G02B 23/24* (2006.01)
*A61B 1/04* (2006.01)
*H04N 5/225* (2006.01)
*G02B 7/09* (2021.01)
*G02B 7/34* (2021.01)
*G02B 23/26* (2006.01)
*A61B 5/107* (2006.01)
*A61B 1/055* (2006.01)

(52) U.S. Cl.
CPC ...... *A61B 1/00009* (2013.01); *A61B 1/00039* (2013.01); *A61B 1/00045* (2013.01); *A61B 1/00105* (2013.01); *A61B 1/00126* (2013.01); *A61B 1/00188* (2013.01); *A61B 1/042* (2013.01); *G02B 7/09* (2013.01); *G02B 23/2453* (2013.01); *G02B 23/2484* (2013.01); *H04N 5/2251* (2013.01); *H04N 5/232* (2013.01); *H04N 5/23212* (2013.01); *H04N 5/23245* (2013.01); *H04N 5/232123* (2018.08); *A61B 1/055* (2013.01); *A61B 5/1076* (2013.01); *G02B 7/34* (2013.01); *G02B 23/26* (2013.01); *G06T 2207/10068* (2013.01)

(58) Field of Classification Search
CPC . A61B 1/0005; A61B 1/0002; A61B 1/00039; A61B 1/00045; A61B 1/00188; A61B 5/1076; A61B 1/055; G02B 23/2484; G02B 23/2453; G02B 7/09; G02B 7/34; G02B 23/26; H04N 5/23212; H04N 5/232; H04N 5/2251; H04N 5/232123; H04N 5/23245; G06T 2207/10068
USPC .................................................. 250/201.2
See application file for complete search history.

(56) References Cited

U.S. PATENT DOCUMENTS

| | | | |
|---|---|---|---|
| 2006/0192886 | A1 | 8/2006 | Kobayashi |
| 2014/0300716 | A1 | 10/2014 | Tsuruoka |
| 2016/0234427 | A1 | 8/2016 | Yoshino |
| 2016/0324398 | A1 | 11/2016 | Sasaki |
| 2018/0007256 | A1* | 1/2018 | Yoshino .................. G02B 7/38 |

FOREIGN PATENT DOCUMENTS

| | | |
|---|---|---|
| JP | 2002-253488 A | 9/2002 |
| JP | 2004-205982 A | 7/2004 |
| JP | 2006-208818 A | 8/2006 |
| JP | 2009-142586 A | 7/2009 |
| JP | 2013-043007 A | 3/2013 |
| JP | 2013-146289 A | 8/2013 |
| WO | 2015/098218 A1 | 7/2015 |
| WO | 2015/111560 A1 | 7/2015 |

* cited by examiner

IMAGE CAPTURING DEVICE, ENDOSCOPE APPARATUS, AND METHOD FOR OPERATING IMAGE CAPTURING DEVICE

CROSS REFERENCE TO RELATED APPLICATION

This application is a continuation of International Patent Application No. PCT/JP2015/080261, having an international filing date of Oct. 27, 2015, which designated the United States, the entirety of which is incorporated herein by reference.

BACKGROUND

The present invention relates to an image capturing device, an endoscope apparatus, a method for operating an image capturing device, and the like.

A depth of field as deep as possible is required for an endoscope system so that a physician can easily perform diagnosis and treatment. In recent years, the depth of field of an endoscope system has become shallow along with the use of an image sensor having a large number of pixels. Thus, detailed focus adjustment is required. In view of this, an endoscope system that performs auto focus (hereinafter, AF) control has been proposed.

Generally, the AF control is for controlling the focus lens to bring an object, within an AF area set on an image, into focus. Thus, a target area that is a part of an object with a certain amount of depth, and a target area that is difficult to be in an AF area might failed to be brought into focus. In view of this, an endoscope system may be capable of switching between the AF mode and a manual focus (hereinafter, referred to as MF) mode. Such an endoscope system brings a target area, which is difficult to bring into focus with the AF control, into focus with a user performing MF adjustment.

JP-A-2001-013398 discloses a camera system that switches the AF mode to the MF mode in response to an operation on an MF operation member by a user, when the target area is difficult to bring into focus with the AF control. In the invention disclosed in JP-A-2001-013398, after the AF mode has been switched to the MF mode with the user operating the MF operation member, the focus control mode returns to the AF mode when half pressing on a release button is released.

JP-A-2013-146289 discloses an endoscope system that includes a scene change detection section and switches the MF mode to the AF mode when a scene change is detected while the system is in the MF mode.

SUMMARY

According to one aspect of the invention, there is provided an image capturing device comprising a processor including hardware the processor being configured to implement:

a switching control process for switching between a manual focus mode of performing manual focus control and an auto focus mode of performing auto focus control; a process for controlling driving of a focus lens of an image capturing section;

a scene status determination process for performing a detection process for detecting a scene change during the manual focus mode and an estimation process for estimating distance change information indicating distance change between the image capturing section and an object;

controlling the driving of the focus lens based on lens drive information input by a user through a focus lens operation section in the manual focus mode;

switching control for switching from the manual focus mode to the auto focus mode when the scene change is detected by the scene status determination process; and controlling the driving of the focus lens to bring the object into focus based on the distance change information estimated by the scene status determination process in the auto focus mode.

According to another aspect of the invention, there is provided an endoscope apparatus comprising the image capturing device.

According to another aspect of the invention, there is provided a method for operating an image capturing device, the method comprising:

performing a switching control process for switching between a manual focus mode of performing manual focus control and an auto focus mode of performing auto focus control;

performing a process for controlling driving of a focus lens of an image capturing section;

performing a detection process for detecting a scene change during the manual focus mode;

performing an estimation process for estimating distance change information indicating distance change between the image capturing section and an object;

controlling the driving of the focus lens based on lens drive information input by a user through a focus lens operation section in the manual focus mode;

performing switching control for switching from the manual focus mode to the auto focus mode when the scene change is detected; and controlling the driving of the focus lens to bring the object into focus based on the distance change information in the auto focus mode.

DESCRIPTION OF EXEMPLARY EMBODIMENTS

Figure 1:
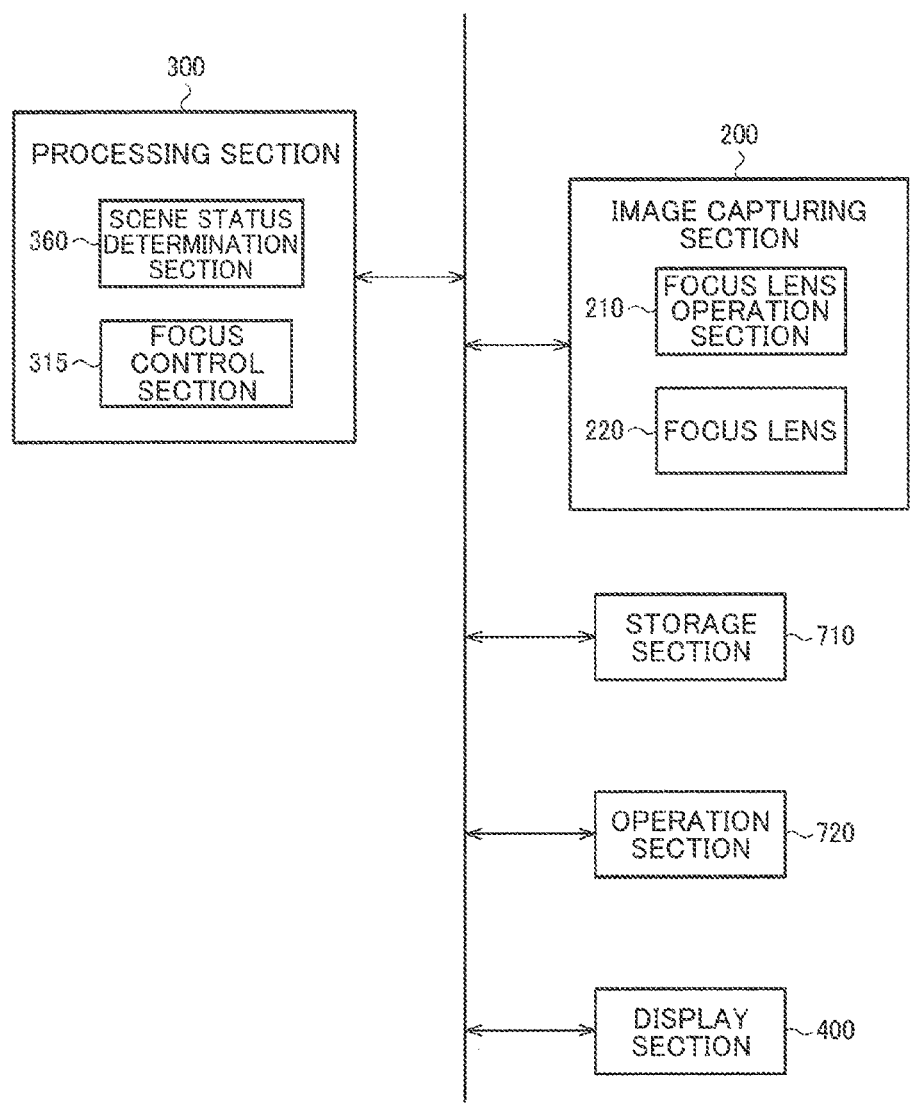
FIG. 1 illustrates a configuration example of an image capturing device.

An embodiment of the present invention relates to an image capturing device including a processor including hardware, the processor being configured to implement: a switching control process for switching between a manual focus mode of performing manual focus control and an auto focus mode of performing auto focus control; a process for controlling driving of a focus lens of an image capturing section; a scene status determination process for performing a detection process for detecting a scene change during the manual focus mode and an estimation process for estimating distance change information indicating distance change between the image capturing section and an object; controlling the driving of the focus lens based on lens drive information input by a user through a focus lens operation section in the manual focus mode; switching control for switching from the manual focus mode to the auto focus mode when the scene change is detected by the scene status determination process; and controlling the driving of the focus lens to bring the object into focus based on the distance change information estimated by the scene status determination process in the auto focus mode.

Another embodiment of the present invention relates to an endoscope apparatus including the image capturing device.

A still another embodiment of the present invention relates to a method for operating an image capturing device, the method including: performing a switching control process for switching between a manual focus mode of performing manual focus control and an auto focus mode of performing auto focus control; performing a process for controlling driving of a focus lens of an image capturing section; performing a detection process for detecting a scene change during the manual focus mode; performing an estimation process for estimating distance change information indicating distance change between the image capturing section and an object; controlling the driving of the focus lens based on lens drive information input by a user through a focus lens operation section in the manual focus mode; performing switching control for switching from the manual focus mode to the auto focus mode when the scene change is detected by the scene status determination process; and controlling the driving of the focus lens to bring the object into focus based on the distance change information estimated by the scene status determination process in the auto focus mode.

The present embodiment will be described below. Note that the following exemplary embodiments do not in any way limit the scope of the invention laid out in the claims. Note also that not all of the elements described below in connection with the exemplary embodiments should be taken as essential elements of the invention.

An image capturing device is described below as an example of a surgical endoscope apparatus. However, the present invention is not limited to this, and can be applied to various image capturing devices (such as endoscope apparatuses for digestive organs and for industrial use, a microscope, a digital video camera, a digital still camera, and a mobile phone with a camera, for example).

1. Image Capturing Device

As described above, a purpose of switching a focus control mode to an auto focus (hereinafter, referred to as AF) mode in response to scene change is to reduce a user operation load. However, the resultant AF control might take more time than manual focus (MF) control. In such a case, a user might switch back to the MF control instead of waiting until focus control is completed for example, resulting in no reduction of the user operation load. Furthermore, even when the focus control mode is not switched to the MF mode, an operation such as surgery might stop during a wait time until the focus control is completed. In view of this, the wait time should be as short as possible. Thus, to facilitate the user operations, a target area of an object needs to be brought into focus (a focusing operation needs to be completed) before the MF control is performed after a focus control mode has switched to the AF mode.

FIG. 1 illustrates a configuration example of an image capturing device that can address such an issue. The image capturing device includes a processing section 300, an image capturing section 200, a storage section 710, an operation section 720, and a display section 400. The processing section 300 at least includes a scene status determination section 360 and a focus control section 315.

The processing section 300 (processor) controls various sections of the image capturing device, and performs various types of information processing such as image processing. The processing section 300 is a processor including hardware as described later, for example.

For example, the storage section 710 (memory) stores image data corresponding to an image captured by the image capturing section 200, setting data on the image capturing device, and the like. The storage section 710 may also be used as a temporally storage memory (working memory) for the processing section 300.

For example, the image capturing section 200 captures an image (movie, still image) and may include an image sensor, an optical system, a driving device that drives a focus mechanism of the optical system, and the like.

The operation section 720 is an input device enabling the user to operate the image capturing device, and may include a button, a lever, a rotation ring, a mouse, a keyboard, a touch panel, and the like. The operation section 720 may serve as a focus lens operation section 210 described later with reference to FIG. 2 and a lock operation section 260 described later with reference to FIG. 12A to FIG. 12D. In such cases, the operation section 720 is provided in the image capturing section 200. However, the present embodiment is not limited to this. The user is an operator of an endoscope system.

The display section 400 (display, display monitor) is a display device that displays a captured image captured by the image capturing section 200 and an image as a result of processing performed by the processing section 300. Examples of the display section 400 include a liquid crystal display device, an electro-luminescence (EL) display device, and the like. The image captured by the image capturing section 200 is hereinafter referred to as a captured image.

The configuration of the image capturing device and an endoscope apparatus including the same is not limited to the configuration illustrated in FIG. 1, and can be modified in various ways by omitting some of the components or adding other components.

An operation of the image capturing device according to the present embodiment is described below.

The image capturing device according to the present embodiment includes the focus control section 315 and the scene status determination section 360.

The focus control section 315 performs a switching control process for switching the focus control mode between an MF mode of performing the MF control and an AF mode of performing the AF control, and performs a process of controlling driving of a focus lens 220 of the image capturing section 200.

The scene status determination section 360 performs a process of detecting a change in a scene during the MF mode, and a process for estimating distance change information indicating distance change between the image capturing section 200 and an object. For example, when the scene change is detected, the scene status determination section 360 estimates the distance change information indicating the distance change, during a scene change detection period that is a predetermined period until the scene change is detected.

In the MF mode, the focus control section 315 controls driving of the focus lens 220 based on lens drive information input by the user through the focus lens operation section 210.

When the MF mode is set, the focus control section 315 performs the switching control to switch the focus control mode from the MF mode to the AF mode in response to the detection of the scene change by the scene status determination section 360.

In the AF mode, the focus control section 315 controls the driving of the focus lens 220 to bring the object into focus, based on the distance change information estimated by the scene status determination section 360 (in the MF mode). For example, the focus control section 315 determines an initial control parameter at the start of the AF control based on the estimated distance change information, and controls the driving of the focus lens 220 based on the initial control parameter thus determined.

More specifically, the focus control section 315 determines at least one of initial control parameters at the start of the AF control including: a target movement direction, a target movement amount, a target position, and an AF control scheme, based on the distance change information. Then, the focus control section 315 performs the AF control based on the initial control parameter thus determined. For example, when the target movement direction is determined as the initial control parameter, the focus control section 315 can move the focus lens 220 in a direction corresponding to the distance change between the image capturing section 200 and the object.

For example, without such a process, the focus lens 220 might be accidentally moved in a direction opposite to the direction corresponding to the distance change between the image capturing section 200 and the object at the start of the AF control. In such a case, the focus lens 220 is moved in the wrong direction until the direction in which the focus lens 220 is moving is determined to have been wrong, and then, the focus lens 220 is moved in the correct direction, resulting in a long period of time required until an in-focus state is achieved. The present embodiment ensured quick completion of the focusing operation quickly completed in such a situation.

As described above, the AF control is performed by using the distance change information estimated by the scene status determination section 360 in the MF mode, whereby the AF control can be more quickly performed after the switching to the AF mode in response to the scene change. As a result, a user operation load can be reduced. This process is descried in detail later.

Furthermore, as described above, the initial control parameter for the AF control is obtained based on the distance change information estimated by the scene status determination section 360 in the MF mode. Thus, the focus lens 220 is moved in a direction corresponding to the latest distance change between the image capturing section 200 and the object, whereby the focusing operation can be quickly completed.

The focus control includes auto focus control, manual focus control, control for switching between these modes, and represents the entire process for controlling the focusing operation by the image capturing section 200.

The auto focus control (AF control) is focus control automatically performed by the image capturing device so that no user operation is required. A focus control mode for setting the AF control to be performed is referred to as the AF mode. The AF control may be performed based on determining the focusing direction by a contrast method (hill climbing), wobbling, or the like.

The manual focus control (MF control) is focus control performed by driving the focus lens based on a user operation. A focus control mode for setting the MF control to be performed is referred to as the MF mode. The focus control mode is a mode for setting any one of the AF control and the MF control to be performed. Thus, any one of the AF mode and the MF mode may be set as the focus control mode.

Possible scene change includes a scene involving a change in the relative distance between the image capturing section 200 and the object, a scene involving a change in a monitoring portion due to a user operation, and the like. The scene involving a change in the monitoring portion is not a scene where the shape or the color of the monitoring portion changes but is a scene where the monitoring portion changes from a first portion to a second portion due to a user operation or the like. Note that a scene where a single monitoring portion has the shape or the like changing so that the in-focus object plane position changes can be regarded as the scene change described above.

The distance change information indicates distance change between the image capturing section 200 and the object in the scene change detection period. For example, the distance change information indicates the direction of the distance change between the image capturing section 200 and the object, the amount of the distance change, the position of the object relative to the image capturing section 200 after the distance change, and the like. The scene change detection period is a predetermined period until the scene change is detected.

The lens drive information is information for instructing the movement of the focus lens 220, and is information for designating the movement direction, the movement amount, the movement position, and the like of the focus lens 220. The lens drive information is input by the user through the focus lens operation section 210 as described later.

The initial control parameter is a control parameter used for starting the AF control. Examples of the initial control parameter include a target movement direction, a target movement amount, and a target position of the focus lens 220, as well as information for designating the AF control scheme or the like. Note that the AF control may be performed based on various parameters for actually driving the focus lens 220 calculated based on the initial control parameter.

The present embodiment may employ the following configuration. Specifically, the image capturing device includes: a memory (storage section 710) that stores information (for example, a program and various types of data); and a processor (processing section 300, processor including hardware) that operates based on the information stored in the memory. In the MF mode, the processor controls the driving of the focus lens 220 based on the lens drive information input by the user through the focus lens operation section 210, performs the switching control to switch the focus control mode from the MF mode to the AF mode when the scene change is detected, and controls the driving of the focus lens 220 to bring the object into focus based on the distance change information.

For example, the functions of the section of the processor (processing section 300) may each be implemented by individual hardware or may be implemented by integrated hardware. The processor may be a central processing unit (CPU), for example. Note that the processor is not limited to the CPU. Various other processors such as a graphics processing unit (GPU) or a digital signal processor (DSP) may also be used. The processor may be a hardware circuit that includes an application specific integrated circuit (ASIC). The memory (storage section 710) may be a semiconductor memory (e.g., SRAM or DRAM), or may be a register. The memory may be a magnetic storage device such as a hard disk drive (HDD), or may be an optical storage device such as an optical disc device, for example. For example, the memory stores a computer-readable instruction, and the function of each section of the processing section 300 is implemented by causing the processor to perform the instruction. The instruction may be an instruction set that is included in a program, or may be an instruction that instructs the hardware circuit included in the processor to operate.

For example, operations according to the present embodiment are implemented as follows. Specifically, the image capturing section 200 captures an image (captured image), and image data thus obtained is processed by the processing section 300 (processor) and then is stored in the storage section 710 (memory). The processing section 300 reads the captured image from the storage section 710, obtains a feature amount (for example, a luminance or the like) of the captured image thus read, and stores the feature amount thus obtained in the storage section 710. The scene status determination section 360 reads the feature amount of the captured image from the storage section 710, performs an estimation process for estimating the distance change information indicating the distance change between the image capturing section 200 and the object based on the feature amount thus read, and stores the distance change information thus estimated in the storage section 710. The focus control section 315 reads the distance change information from the storage section 710, and controls the driving of the focus lens 220 based on the distance change information thus read. The focus control section 315 determines the initial control parameter at the start of the AF control based on the distance change information read from the storage section 710, and stores the initial control parameter thus determined in the storage section 710. The focus control section 315 reads the initial control parameter from the storage section 710, and performs the AF control based on the initial control parameter thus read.

2. Endoscope Apparatus

A configuration and an operation in a case where the image capturing device described above is applied to an endoscope apparatus (surgical endoscope apparatus, endoscope system) are described in detail below.

2.1. System Configuration Example

Figure 2:
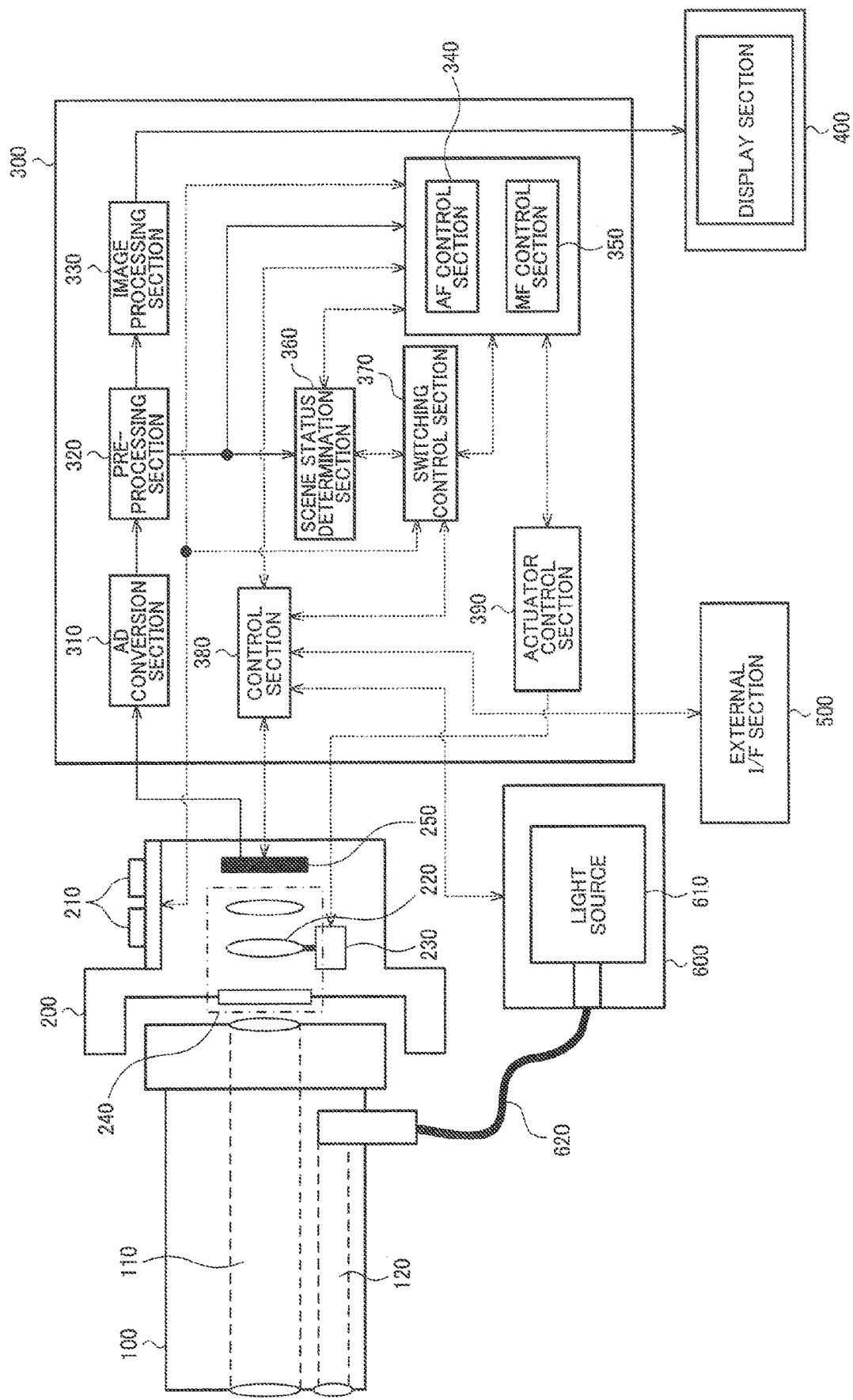
FIG. 2 illustrates a configuration example of an endoscope apparatus.

FIG. 2 illustrates an example of a configuration of the endoscope apparatus. The endoscope apparatus according to the present embodiment illustrated in FIG. 2 includes a rigid scope 100 inserted into a body, the image capturing section 200 connected to the rigid scope 100, the processing section 300, the display section 400, an external interface (I/F) section 500, and a light source section 600. In FIG. 2, solid lines represent a flow of image data, and dotted lines represent a flow of other control data (control signal). The same applies to FIG. 3, FIG. 4, FIG. 6, FIG. 7, and FIG. 9 described later.

For example, the rigid scope 100, the image capturing section 200, the processing section 300, the display section 400, and the light source section 600 are respectively provided as a rigid scope, a camera head, a video processor (processing device), a display, and a light source device as individual devices. The rigid scope is detachably attached to the camera head with a chuck mechanism provided to the camera head. The camera head, the display, and the light source device are each connected to the video processor via a cable. The rigid scope is connected to the light source device via a light guide cable. Note that the configuration of the image capturing device and the endoscope apparatus is not limited to this.

For example, the endoscope apparatus using the rigid scope 100 is used for surgery such as laparoscopic surgery. Specifically, a small hole is perforated in an abdominal area of a living body, the rigid scope 100 is inserted through the small hole, a surgical tool is inserted through the small hole or another small hole, and a surgical process using the surgical tool within a field of view of the rigid scope 100 is performed. For example, the surgical tool includes various tools including a surgical knife, a pair of forceps, a suture needle, a suture, and tools for introducing and absorbing rinsing water. The focus control switching method according to the present embodiment is not limited to the application to the endoscope apparatus using the rigid scope 100, and may be applied to an endoscope apparatus using a flexible scope.

Configurations and operations of the sections are described below.

The light source section 600 includes a white light source 610 that emits white light, and a light guide cable 620 that guides the light, emitted from the white light source 610, to the rigid scope 100.

The rigid scope 100 is inserted into the body. The rigid scope 100 includes a lens system 110 and a light guide section 120. The lens system 110 includes an objective lens, a relay lens, an eyepiece, and the like. The light guide section 120 guides light, emitted from the light guide cable 620, to a distal end of the rigid scope 100.

The image capturing section 200 forms an image from reflected light from the object. The image capturing section 200 includes the focus lens operation section 210, the focus lens 220, a focus lens driver section 230, an objective lens system 240, and an image sensor 250.

The focus lens 220 is a lens for adjusting an in-focus object plane position (focus).

The focus lens driver section 230 drives the focus lens 220. The focus lens driver section 230 is implemented by any desired actuator such as a voice coil motor (VCM), for example.

The objective lens system 240 forms an optical image from reflected light that is light emitted from the light guide section 120 and reflected on the object (forms an optical image of the object).

The image sensor 250 photoelectrically converts the reflected light for forming the optical image with the objective lens system 240 from the reflected light (object image) into an image. The image sensor 250 is a primary color Bayer image sensor in which any of R, G, and B color filters is disposed in a Bayer array, for example. Alternatively, an image sensor that utilizes a complementary color filter, a stacked image sensor that is designed so that each pixel can receive light having a different wavelength without using a color filter, a monochrome image sensor that does not utilize a color filter, or any other image sensor may be employed as long as the object can be captured to obtain an image.

The focus lens operation section 210 is an interface with which the user directly operates the focus lens 220. The lens drive information can be input by operating the focus lens operation section 210. The user operates the focus lens operation section 210 to drive the focus lens 220 to adjust the in-focus object plane position. For example, as illustrated in FIG. 2, the focus lens operation section 210 includes a button for moving the focus toward the near point side and a button for moving the focus toward the far point side. Alternatively, the interface may be a focus ring, a mouse wheel, or a click wheel.

The in-focus object plane position is a position at which the object is brought into focus by the image capturing section 200. Specifically, the in-focus object plane position (or the object side focal point) is determined in accordance with an imaging plane (or an image side focal point) on the objective lens system 240. The in-focus object plane position is a position of the focus object plane achieving a state where the image plane matches the imaging plane of the image sensor 250. The in-focus object plane position is based on the positional relationship between the image capturing section 200 and the focus object plane, and is represented by a distance between a reference point of the image capturing section 200 (for example, a distal end of the objective lens system 240, a distal end of the rigid scope 100, or the like) and the focus object plane (an in-focus plane on the object side of the optical system). For example, the in-focus object plane position can be obtained based on control information (position) on the focus lens 220 and the optical characteristics (design value) of the objective lens system 240 and the lens system 110 of the rigid scope 100.

The processing section 300 performs signal processing including image processing. The processing section 300 includes an AD conversion section 310, a pre-processing section 320, an image processing section 330, an AF control section 340, an MF control section 350, the scene status determination section 360, a switching control section 370, a control section 380, and an actuator control section 390. The processing section 300 is a processor including hardware as described later, for example. The focus control section 315 as illustrated in FIG. 1 corresponds to the AF control section 340, the MF control section 350, the switching control section 370, and the actuator control section 390.

The AD conversion section 310 converts an analog signal output from the image sensor 250 into a digital signal.

The pre-processing section 320 performs image processing on an image output from the AD conversion section 310. The image processing includes an optical black correction process (OB process), an interpolation process (demosaicing process), and a conversion process (from an RGB signal to a YC signal).

The image processing section 330 performs image processing including a color conversion process, a gray scale conversion process, an edge enhancement process, a scaling process, a noise reduction, and the like.

The AF control section 340 performs the AF control based on an image output from the pre-processing section 320. For example, the AF control is performed based on a contrast value calculated from a signal indicating a luminance (Y) of the image. For example, the AF control may be performed based on a known method such as wobbling, hill climbing, or scanning. The AF control may also be performed by using phase information obtained by an image plane phase sensor provided to the image sensor 250.

The MF control section 350 performs the MF control based on drive information (such as driving direction or speed) on the focus lens, output from the focus lens operation section 210 in accordance with a user operation.

The scene status determination section 360 detects the scene change based on the image output (acquired) from the pre-processing section 320. For example, the scene status determination section 360 may detect the scene change based on images output from the AD conversion section 310, the image processing section 330, and any other appropriate part (including the sections of the processing section 300). A specific configuration of the scene status determination section 360 is described later with reference to FIG. 3 and FIG. 4.

The switching control section 370 determines whether the currently set focus control mode is the AF mode or the MF mode, and performs switching control for the modes.

The control section 380 is mutually connected to the sections of the processing section 300 (mainly including the AF control section 340, the MF control section 350, the switching control section 370, and the like), the image sensor 250, the external I/F section 500, the light source section 600, and the like to exchange control signals.

The actuator control section 390 outputs a driving signal for an actuator (focus lens driver section 230) in accordance with control information, for the actuator, output from the AF control section 340 or the MF control section 350.

The display section 400 (display, display monitor) is a display device that displays an image captured by the image capturing section 200 and an image as a result of the processing performed by the processing section 300. Examples of the display section 400 include a liquid crystal display device, an electro-luminescence (EL) display device, and the like.

The external I/F section 500 is an interface that allows the user to perform an input operation on the endoscope apparatus and the like. For example, the external I/F section 500 includes a setting button for setting the position and the size of the AF area, and an adjustment button for adjusting image processing parameter.

2.2. Scene Status Determination Section

Next, an example of a configuration of the scene status determination section 360 is described in detail with reference to FIG. 3 and FIG. 4. The scene status determination section 360 has different configurations for detecting the scene change based on an image feature amount and for detecting the scene change based on a movement of the image capturing section 200.

Figure 3:
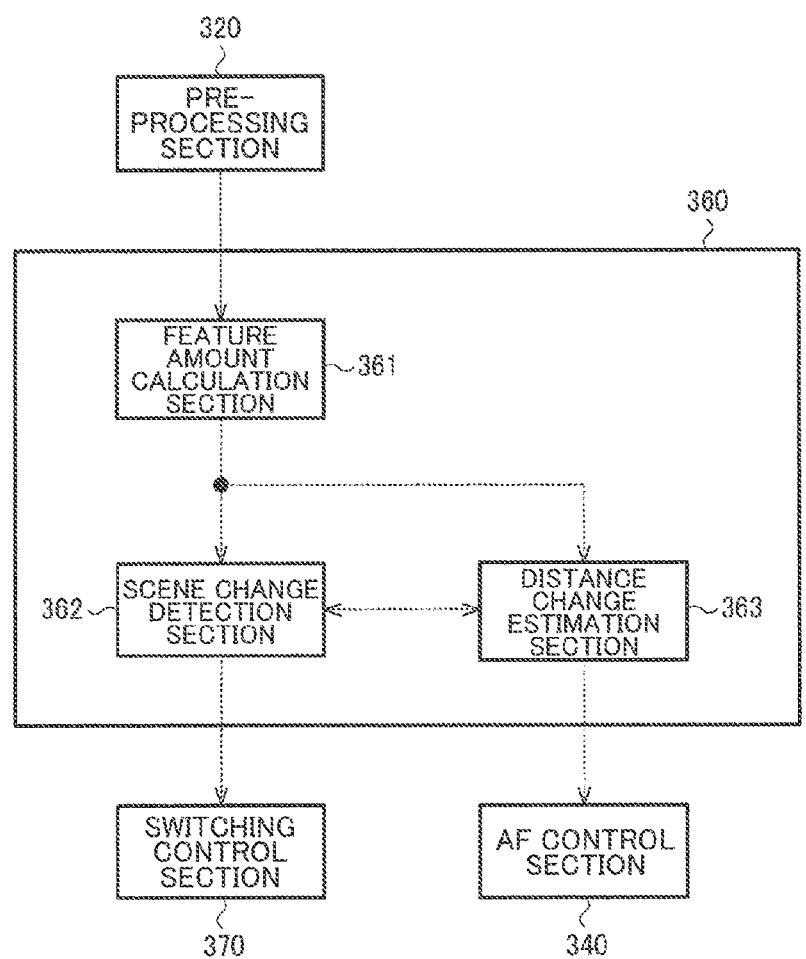
FIG. 3 illustrates a configuration example of the scene status determination section including a feature amount calculation section.

FIG. 3 illustrates the configuration of the scene status determination section 360 for detecting the scene change based on the image feature amount. The scene status determination section 360 with this configuration includes a feature amount calculation section 361, a scene change detection section 362, and a distance change estimation section 363.

In the configuration illustrated in FIG. 3, the scene status determination section 360 performs a scene change detection process and a distance change information estimation process based on a change amount of the feature amount of the captured image captured by the image capturing section 200.

For such processes, for example, the feature amount calculation section 361 calculates the feature amount including a contrast value, a luminance, a color, and the like from the image output from the pre-processing section 320.

The scene change detection section 362 stores a feature amount f1, at a timing when the switching control section 370 performs switching control from the AF mode to the MF mode, in a memory not illustrated in FIG. 3. The scene change detection section 362 detects a scene change when an amount of change (absolute value) from a feature amount f2 during the MF mode to the feature amount f1 thus stored is equal to or larger than a threshold.

The distance change estimation section 363 stores a luminance b1 at a timing of the switching control from the AF mode to the MF mode performed by the switching control section 370, in the memory not illustrated in FIG. 3. The distance change estimation section 363 compares a luminance b2 at the scene change detection timing and the luminance b1 thus stored, to estimate the direction of the distance change between the image capturing section 200 and the object. In this process, for example, the distance change estimation section 363 estimates that a distance between the image capturing section 200 and the object has decreased when the luminance b2 at the scene change detection timing is larger. The distance change estimation section 363 may estimate the direction and the amount of the distance change by using a level of the luminance change.

Thus, for example, the scene change detection, the distance change estimation, and the like can be implemented without an acceleration sensor or the like.

In the process described above, the scene status determination section 360 (scene change detection section 362) may determine that the scene change has occurred when the change amount of the feature amount of the captured image keeps exceeding a given threshold for a given time period or longer.

Thus, for example, a quickly corrected distance change, which only occurred for only a short period of time due to an erroneous user operation or the like, can be prevented from being erroneously detected as the scene change.

As described above, the scene status determination section 360 may perform the scene change detection process and the distance change information estimation process based on the amount of change in the luminance serving as the feature amount of the captured image.

Specifically, for example, the scene change detection section 362 may detect the scene change when the change amount of the luminance of the captured image exceeds a threshold. The distance change estimation section 363 may obtain the distance change information on the direction of a luminance change when the scene change is detected (changed to be brighter or darker) and the amount of change in the luminance. For example, the AF control section 340 may determine the movement direction of the focus lens 220 at the start of the AF control based on the information on the direction of the luminance change thus obtained, and may determine the movement amount of the focus lens 220 at the start of the AF control based on the information on the change amount of the luminance thus obtained.

Thus, the scene change and the distance change can be prevented from erroneously detected, even when the color of the monitoring portion of the object changes due to a surgery (treatment). When scene change is detected, the distance change information can be estimated based on the information (luminance) used for detecting the scene change. Thus, high speed AF control can be implemented, based on the distance change information, after the focus control mode is switched to the AF mode.

The endoscope apparatus is used not only for monitoring lesioned parts but is also used for treating lesioned parts. Such a case involves a large change in the feature amount (such as a contrast value, a luminance, or a color) of the image, resulting in erroneous detection of a scene change. The user does not largely move the image capturing section 200 during the treatment. Thus, once the object is in focus as a result of the AF control, the AF control needs not to be performed again as long as there is no scene change. During the treatment, a physician performs a delicate work while checking a displayed image, and thus the AF should not be performed for the sake of display image stabilization. In other words, when a scene change that is actually not a scene change is detected, the AF control is unnecessarily performed, to make the display image blurred during the AF control. This results in a risk of hindering the treatment.

Figure 4:
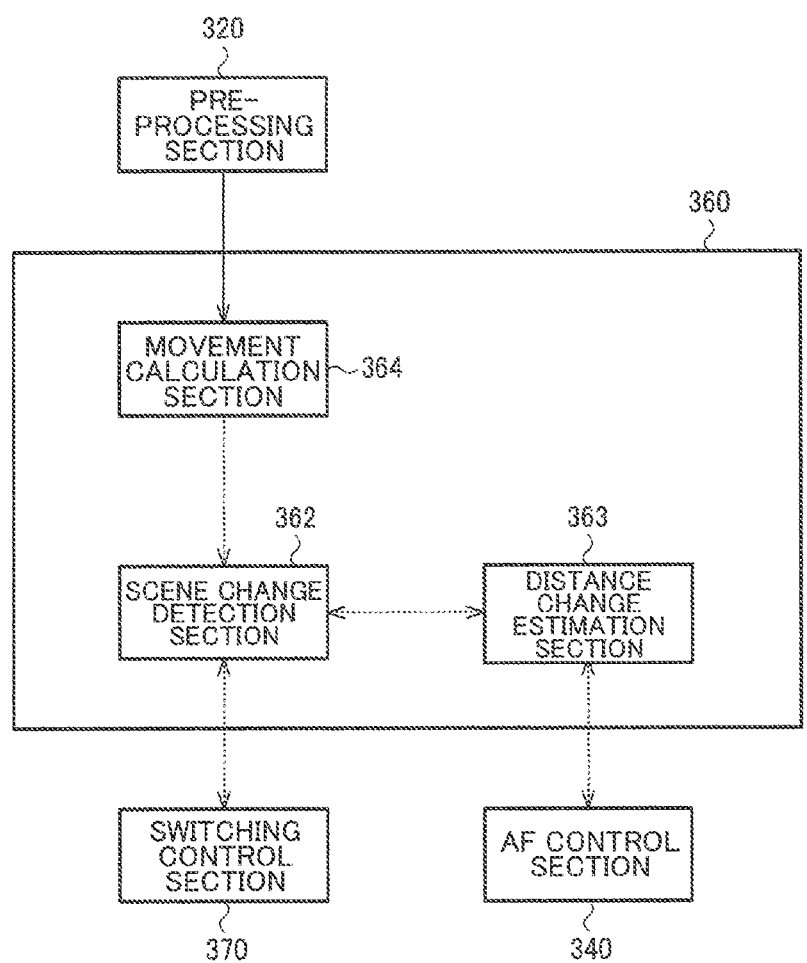
FIG. 4 illustrates a configuration example of the scene status determination section including a movement calculation section.

FIG. 4 illustrates a configuration of the scene status determination section 360 for preventing such an operation. The scene status determination section 360 illustrated in FIG. 4 detects a scene change based on the movement of the image capturing section 200. The scene status determination section 360 with this configuration includes a movement calculation section 364, the scene change detection section 362, and the distance change estimation section 363.

The scene status determination section 360 with the configuration illustrated in FIG. 4 performs the scene change detection process and the distance change information estimation process based on the movement of the image capturing section 200.

Specifically, for example, the movement calculation section 364 calculates a motion vector between a current image and a past image, using images output from the pre-processing section 320. The past image is an image captured in a frame that is immediately before the frame of the current image for example. However, the present embodiment is not limited to this. The movement calculation section 364 calculates the movement of the image capturing section 200 (such as a movement in the optical axis direction, a movement orthogonal to the optical axis direction, and a movement amount). Specifically, the movement calculation section 364 may calculate a single motion vector from the image, and calculate the movement of the image capturing section 200 using this vector, or may calculate a plurality of motion vectors from any appropriate area set in the image, and calculate the movement of the image capturing section 200 by performing an overall judgment on the resultant vectors. For example, the movement calculation section 364 may calculate the movement of the image capturing section 200 by using an unillustrated acceleration sensor.

The scene change detection section 362 detects a scene change when the movement amount of the image capturing section 200 is determined to be equal to or larger than a threshold.

The movement amount changes in accordance with a change in positional relationship between the image capturing section 200 and the object (a movement with no change in the optical axis direction of the camera for example), or a change in relative orientations of the image capturing section 200 and the object (rotation involving a change in the optical axis direction of the camera (pan, tilt) for example). For example, the magnitude and the direction of a motion vector, detected from an image, change in accordance with the movement and the rotation of the image capturing section 200. Alternatively, the motion sensor may be used to obtain acceleration, angular acceleration, angular velocity, and the like based on the movement or the rotation of the image capturing section 200. The movement amount is a value indicating information on one of the magnitude and the direction of the movement or both In this configuration, the distance change estimation section 363 estimates the direction and the amount of the distance change between the image capturing section 200 and the object, by using the movement amount in the optical axis direction that is one of the movement amounts of the image capturing section 200 used for the scene change detection by the scene change detection section 362.

For example, with the scene change detection section 362 detecting the scene change based on the movement amount of the image capturing section 200, a scene involving a partial change in the shape, the color, or the like of the object (for example, a lesioned part) due to the treatment can be prevented from being detected as a scene change. Thus, unnecessary AF control and the like can be prevented.

The scene change detection section 362 obtains the amount of the distance change between the object and the image capturing section 200 based on the information on the movement of the image capturing section 200 acquired from the movement calculation section 364. The scene change detection section 362 detects a scene change when the amount of the distance change thus obtained exceeds a given threshold. The distance change estimation section 363 obtains information on the direction of the distance change (increased or decreased) and the amount of the distance change, when the scene change has been detected by the scene change detection section 362, as the distance change information described above. The AF control section 340 determines the movement direction of the focus lens 220 at the start of the AF control, based on the direction of the distance change thus obtained. The AF control section 340 determines the movement amount of the focus lens 220 at the start of the AF control based on the information on the amount of the distance change thus obtained.

As described above, when a scene change is detected, the information used for detecting the scene change can be used for estimating the distance change information. High speed AF control can be implemented, after the switching to the AF mode, based on the distance change information.

In the configuration illustrated in FIG. 4, the scene status determination section 360 (distance change estimation section 363) performs the distance change information estimation process based on the information obtained in the scene change detection process.

Thus, the scene change detection process and the distance change information estimation process can be partially performed as a common process, whereby reduction of a processing amount and the like can be achieved.

When a scene change occurs, focus adjustment is likely to be required. Thus, when the scene change is detected, the switching control section 370 switches the focus control mode to the AF mode. In such a case, the distance change estimation section 363 can obtain the information on how the relative positional relationship between the object and the image capturing section 200 has changed from a state before the scene change and a state after the scene change based on a result of the scene change detection process. The distance change estimation section 363 performs the distance change information estimation process based on the information obtained in the scene change detection process. Thus, high speed AF control, after the switching to the AF mode, can be implemented with scene change detection process performed in the MF mode effectively used.

In the case described above, the scene status determination section 360 (scene change detection section 362) may determine that the scene change has occurred when the amount of the distance change indicated by the estimated distance change information continuously exceeds a given threshold for a given period of time.

Thus, for example, a quickly corrected distance change, which only occurred for only a short period of time due to an erroneous user operation or the like, can be prevented from being erroneously detected as the scene change.

The scene status determination section 360 (scene change detection section 362) may determine that the scene change has occurred, when an integrated value of the amount of the distance change, indicated by the estimated distance change information, exceeds a given threshold.

Thus, for example, a scene where the image capturing section 200 moves back and forth due to camera shake and the like can be prevented from being detected as the scene change.

2.3. Detail of Process

Figure 5:
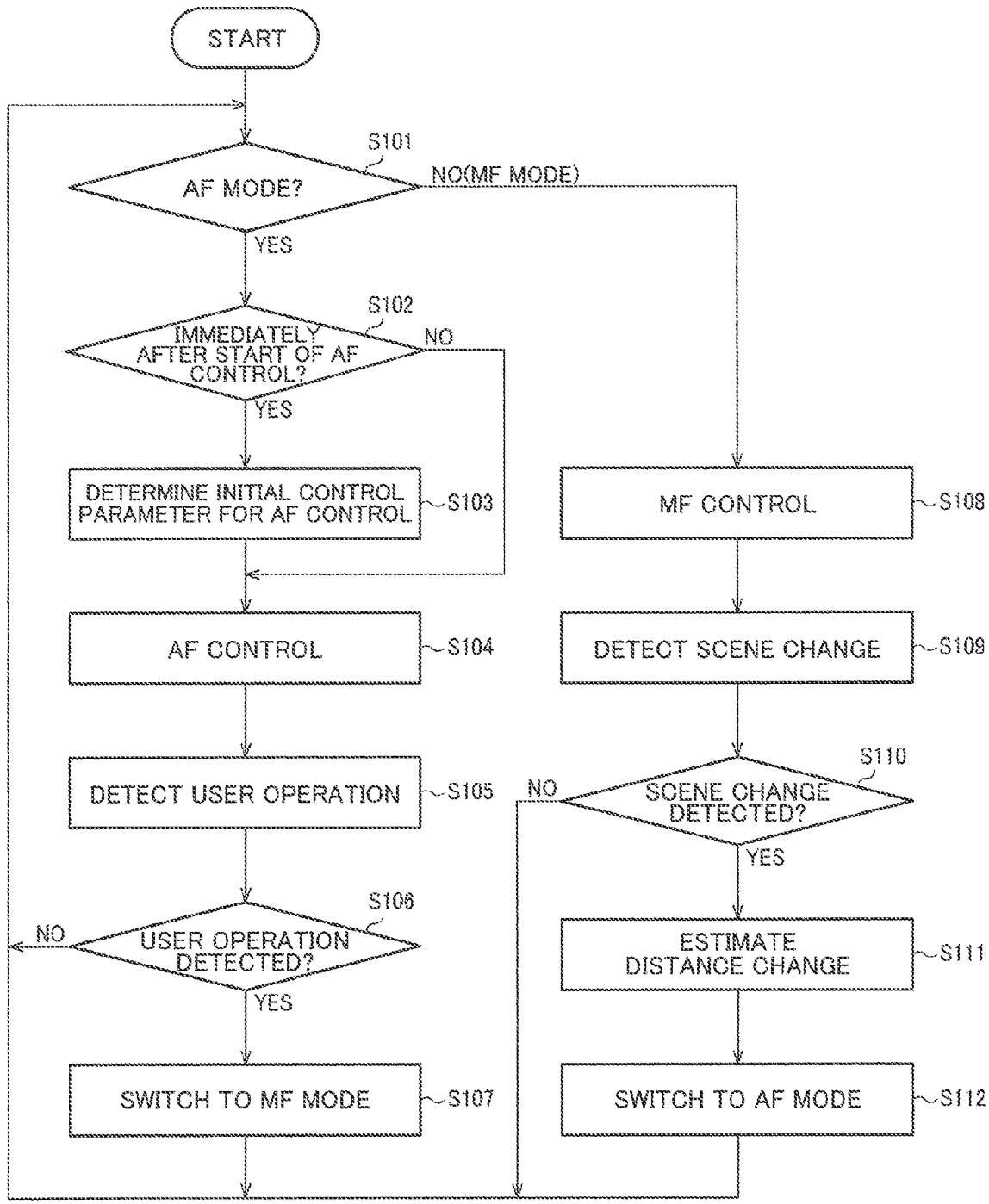
FIG. 5 is a flowchart illustrating a flow of a process according to an embodiment.

Next, the process is described in detail with reference to a flowchart in FIG. 5.

First of all, the switching control section 370 determines which one of the AF mode or the MF mode is the current focus control mode (S101).

When the switching control section 370 determines that the current focus control mode is the AF mode, the AF control section 340 first determines whether the current timing is immediately after the start of the AF control (S102). When the AF control section 340 determines that the current timing is immediately after the start of the AF control, the AF control section 340 sets the initial control parameter for the AF control in a way described later (S103).

Next, the AF control section 340 executes the AF control based on the initial control parameter for the AF control thus set (S104), and outputs the control information on the focus lens 220 to the actuator control section 390. In step S102, when the AF control section 340 determines that the current timing is not immediately after the start of the AF control, the process directly proceeds to step S104.

The switching control section 370 detects information indicating whether the user has operated the focus lens operation section 210, that is, whether the drive information on the focus lens 220 has been output (S105). When the user operation is determined to have been detected (S106), the switching control section 370 switches the focus control mode from the AF mode to the MF mode (S107), and the process returns to step S101. When the user operation is determined to have not been detected (S106), the process directly returns to step S101.

When the switching control section 370 determines that the current focus control mode is the MF mode in step S101, the MF control section 350 performs the MF control (S108). Thus, the MF control section 350 generates the control information for the focus lens 220 based on the drive information on the focus lens 220, and outputs the control information to the actuator control section 390.

The scene status determination section 360 detects a scene change in any of the ways described above (S109). When the scene change is determined to have been detected (S110), the scene status determination section 360 estimates the distance change between the image capturing section 200 and the object in any of the ways described above (S111). Then, the switching control section 370 switches the focus control mode from the MF mode to the AF mode (S112), and the process returns to step S101. When the scene change is determined to have not been detected in step S110, the process directly returns to step S101.

Next, how the initial control parameter for the AF control is set in step S103 described above is described. The initial control parameter for the AF control includes a target movement direction, a target movement amount, and a target position of the focus lens 220, as well as (the type) of the AF control scheme at the start of the AF control. In the present embodiment, the initial control parameter may be obtained as any one or a plurality of the parameters or may be obtained as all of the parameters.

Specifically, the focus control section 315 (AF control section 340) determines the target movement direction of the focus lens 220 as at least one parameter serving as the initial control parameter based on the distance change information. For example, the AF control section 340 obtains information on the direction of the distance change between the image capturing section 200 and the object, based on the distance change information estimated by the scene status determination section 360. The AF control section 340 sets the target movement direction of the focus lens 220 at the AF start timing as the initial control parameter, based on the information on the direction of the distance change thus obtained. For example, when the distance between the image capturing section 200 and the object changes to decrease, the target movement direction of the focus lens 220 is determined to be a direction in which the in-focus object plane position approaches the image capturing section 200.

Thus, the focus lens 220 can move toward the in-focus lens position when the AF control starts. The in-focus lens position is the position of the focus lens 220 achieving the in-focus state, that is, the position of the focus lens 220 at which the object is brought into focus.

The focus control section 315 (AF control section 340) may determine the target movement amount of the focus lens 220 as at least one parameter serving as the initial control parameter, based on the distance change information. For example, the AF control section 340 obtains the amount of the distance change between the image capturing section 200 and the object, based on the distance change information estimated by the scene status determination section 360. The AF control section 340 may set the target movement amount of the focus lens 220 at the start of the AF control as the initial control parameter, based on the amount of the distance change thus obtained. For example, when the distance change between the image capturing section 200 and the object is large, the movement amount of the focus lens 220 is set to be large.

Thus, the focus lens 220 can be moved by a movement amount corresponding to the distance change between the image capturing section 200 and the object at the start of the AF control.

The focus control section 315 (AF control section 340) may determine the target position of the focus lens 220 as at least one parameter serving as the initial control parameter, based on the distance change information. For example, the AF control section 340 obtains information on the direction and the amount of the distance change between the image capturing section 200 and the object, based on the distance change information estimated by the scene status determination section 360. The AF control section 340 may set the target position of the focus lens 220 at the start of the AF control as the initial control parameter, based on the direction and the amount of the distance change thus obtained.

Thus, the target position of the focus lens 220 can be set to be close to the in-focus lens position at the start of the AF control.

The focus control section 315 (AF control section 340) may determine the AF control scheme as at least one parameter serving as the initial control parameter, based on the distance change information. For example, the AF control section 340 obtains the amount of the distance change between the image capturing section 200 and the object, based on the distance change information estimated by the scene status determination section 360. The AF control section 340 may set the (type) of the AF control scheme to be employed as the initial control parameter, based on the amount of the distance change thus obtained. For example, the hill climbing or scanning is set when the distance change between the image capturing section 200 and the object is large, and wobbling is set when the distance change is small.

Thus, the AF control can be performed with the AF control scheme appropriate for the latest distance change.

Through the process described above, the initial control parameter for the AF control can be appropriately set, and high speed and highly accurate AF control can be achieved.

3. First Modification 3.1. Overview

Next, a first modification is described. To begin with, the AF control (AF mode) requires less user operations and thus is less cumbersome for the user than the MF control (MF mode). Thus, the AF control is first performed, and the MF control is performed when the AF control fails to focus as the user intended, as described later in a second modification.

Still, a target area failed to be brought into focus by the AG control in a certain scene, might be capable of being brought into focus by the AF control when the scene changes. As described above, the AF control should be employed, for reducing the user operation load, as long as the target area can be brought into focus.

Thus, in the first modification, the AF control is performed again when the scene changes to be determined to be stable. The stable scene is a state involving no scene change within a given period of time based on the current timing (a certain timing). Specifically, the given period of time may include one of periods before and after the current timing or both.

Figure 6:
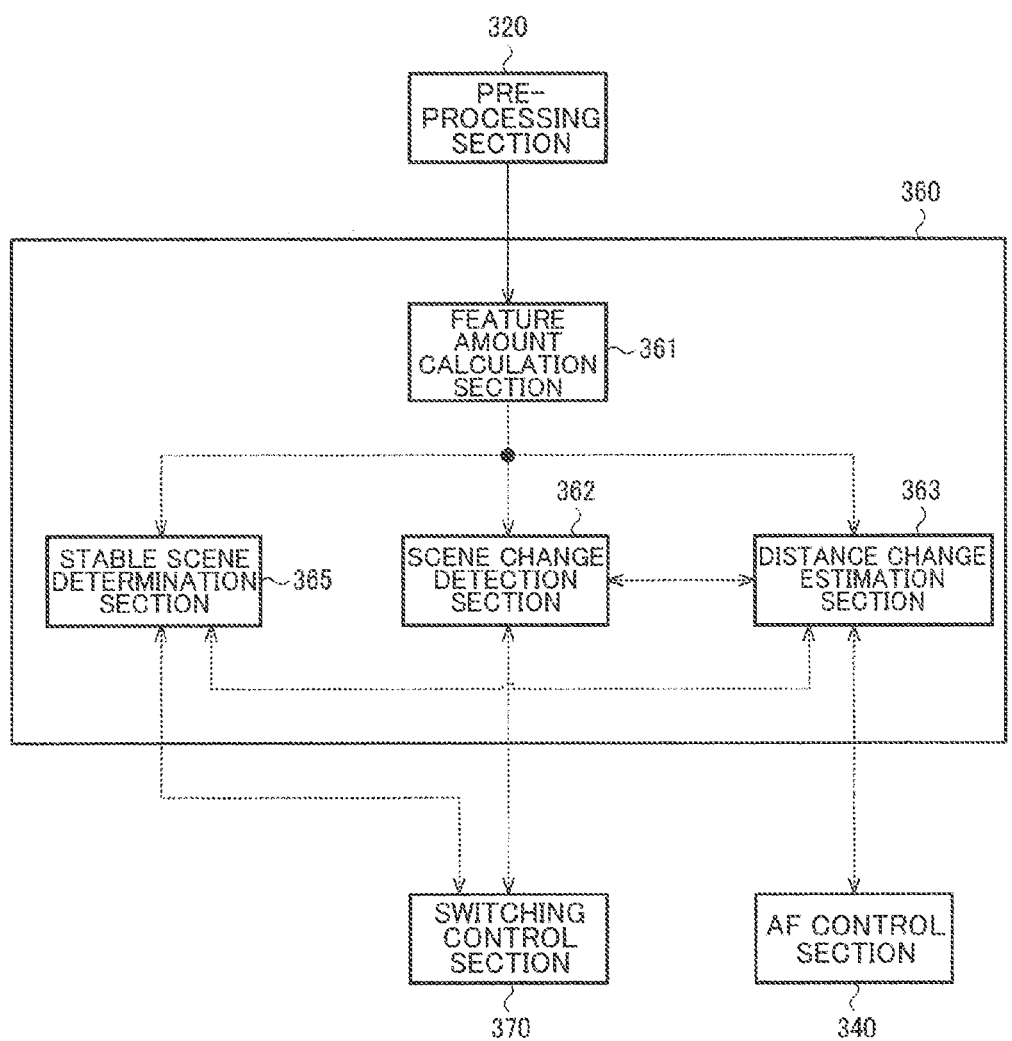
FIG. 6 illustrates a configuration example of a scene status determination section configured to perform stable scene determination.

In the first modification, the scene status determination section 360 includes a stable scene determination section 365 in addition to the configuration described with reference to FIG. 3, as illustrated in FIG. 6.

The stable scene determination section 365 determines whether or not a scene for the image capturing by the image capturing section 200 is stable. The focus control section 315 performs the AF control when the stable scene determination section 365 determines that the scene is stable.

Thus, the AF control is performed when the scene is stable, and thus the operation load of the user can be reduced.

The image capturing section 200 may be operating when the scene change is detected. For example, the AF control performed in a situation under frequent scene change (during the scene change) might result in an erroneous operation and a failure to accurately bring the object into focus. Thus, in this modification, the AF control is performed when the scene is determined to be stable.

Specifically, the stable scene determination section 365 determines whether or not the scene is stable, after the scene status determination section 360 has detected a scene change. The focus control section 315 performs the AF control when the stable scene determination section 365 determines that the scene is stable.

Thus, an erroneous operation due to the AF control can be prevented, and an object can be accurately brought into focus.

3.2. Stable Scene Determination Process

Next, the process of determining whether or not the scene is stable is described in detail. In this first modification, the function of the scene change detection section 362 described above may be implemented as in the following two specific examples. As the first specific example, the stable scene determination section 365 may determine whether or not the scene is stable based on the feature amount of the image. FIG. 6 illustrates a configuration of the scene status determination section 360 according to such an example.

In the example illustrated in FIG. 6, the stable scene determination section 365 stores the feature amount f1 of an image captured in a certain frame, in a memory not illustrated in FIG. 6. The stable scene determination section 365 determines that the scene is stable, when a difference (absolute value) between the feature amount (reference value) f1 thus stored and the feature amount f2 of an image captured in the next frame is equal to or smaller than a threshold. When the stable scene determination section 365 determines that the scene is unstable, when the difference between the two feature amounts (f1 and f2) is larger than the threshold. When the scene is determined to be unstable, the stable scene determination section 365 updates the reference value with the new feature amount f2. The stable scene determination section 365 may determine that the scene is stable when a state where the difference between the two feature amounts (f1 and f2) is larger than the threshold continues for a predetermined period of time or more.

Figure 7:
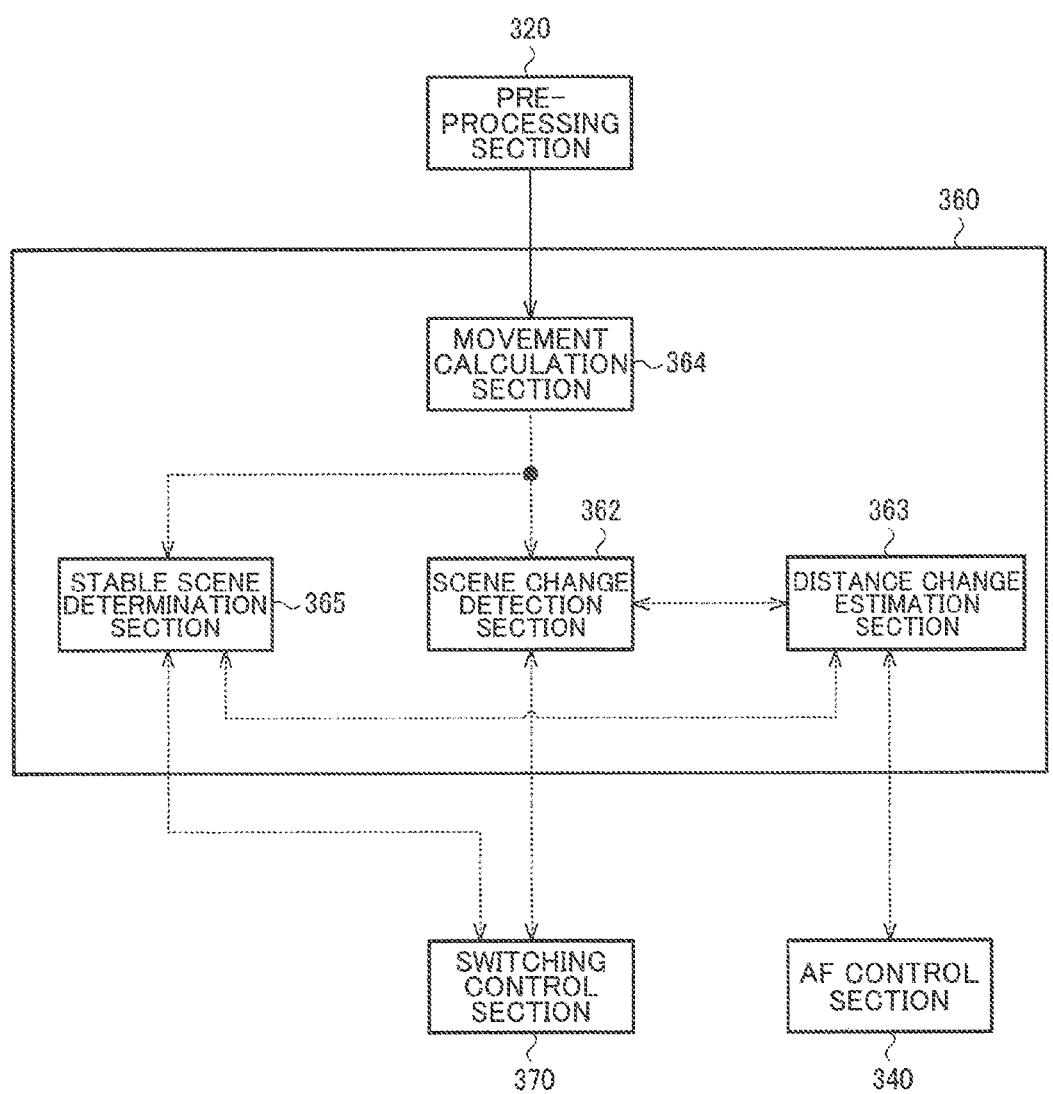
FIG. 7 illustrates another configuration example of a scene status determination section configured to perform stable scene determination.

As the second specific example, the stable scene determination section 365 determines whether or not the scene is stable, based on the movement of the image capturing section 200. FIG. 7 illustrates an example of a configuration of the scene status determination section 360 according to the second example.

In the example illustrated in FIG. 7, the stable scene determination section 365 determines that the scene is stable, when the movement amount of the image capturing section 200 is equal to or smaller than a threshold. The stable scene determination section 365 may determine that the scene is stable when a state where the movement amount of the image capturing section 200 is equal to or smaller than the threshold continues for a predetermined period of time or more. The stable scene determination section 365 may determine that the scene is stable when an integrated value of the movement amounts of the image capturing section 200 within a predetermined period is equal to or smaller than a threshold.

3.3. Detail of Process

Next, a flow of the process according to the first modification is described with reference to FIG. 8. A flow of the process in step S201 to step S209 in FIG. 8 is the same as that of the process in step S101 to step S109 in FIG. 5 described above, and the description thereof is omitted.

Figure 8:
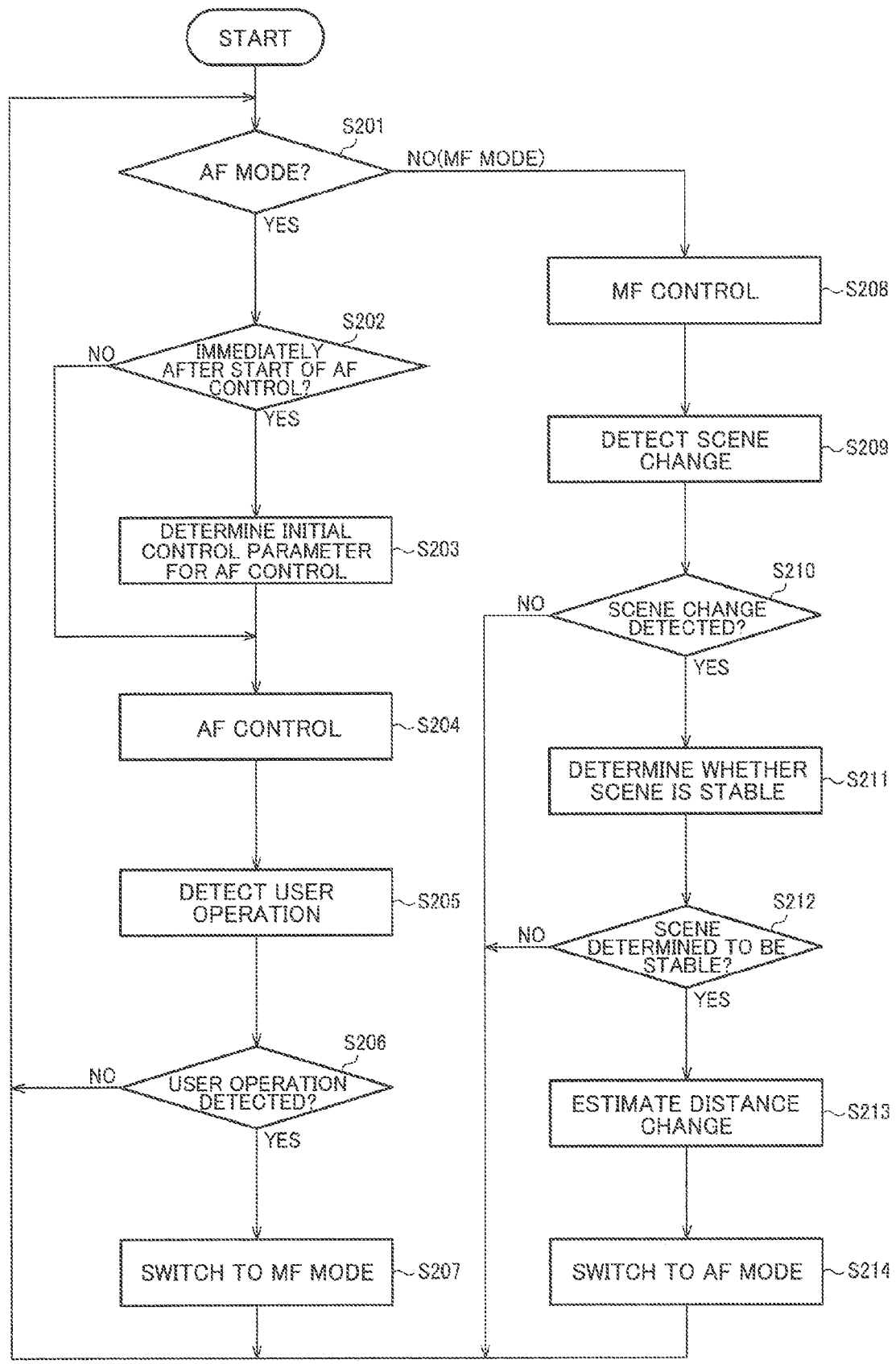
FIG. 8 is a flowchart illustrating a flow of a process according to a first modification.

In the first modification, as illustrated in FIG. 8, when the scene change detection section 362 detects a scene change (S210), the stable scene determination section 365 determines whether or not the scene is stable (S211). For example, the stable scene determination process is performed as described above with reference to FIG. 6 and FIG. 7. When the stable scene determination section 365 determines that the scene is stable (S212), the distance change estimation section 363 estimates the distance change between the image capturing section 200 and the object (S213). In the process, the distance change estimation section 363 may estimate the distance change by using the luminance change and the motion vector between a scene change detection timing and a stable scene detection timing. Then, the switching control section 370 switches the focus control mode from the MF mode to the AF mode (S214), then the process returns to step S201.

When the scene change detection section 362 has not detected the scene change (S210) or when the scene change has been detected but the resultant scene is determined to be unstable by the stable scene determination section 365 (S212), the process directly returns to step S201.

4. Second Modification 4.1. Overview

Next, a second modification is described. As described above, the AF control (AF mode) involves a less operation load on the user than the MF control (MF mode). Thus, the AF control is less cumbersome for the user. However, when the object cannot be brought into focus as the user intended with the AF control, the object can be more favorably brought into focus with the MF control.

Thus, in the second modification, the MF control is performed when it is determined that the object is difficult to bring into focus with the AF control.

Figure 9:
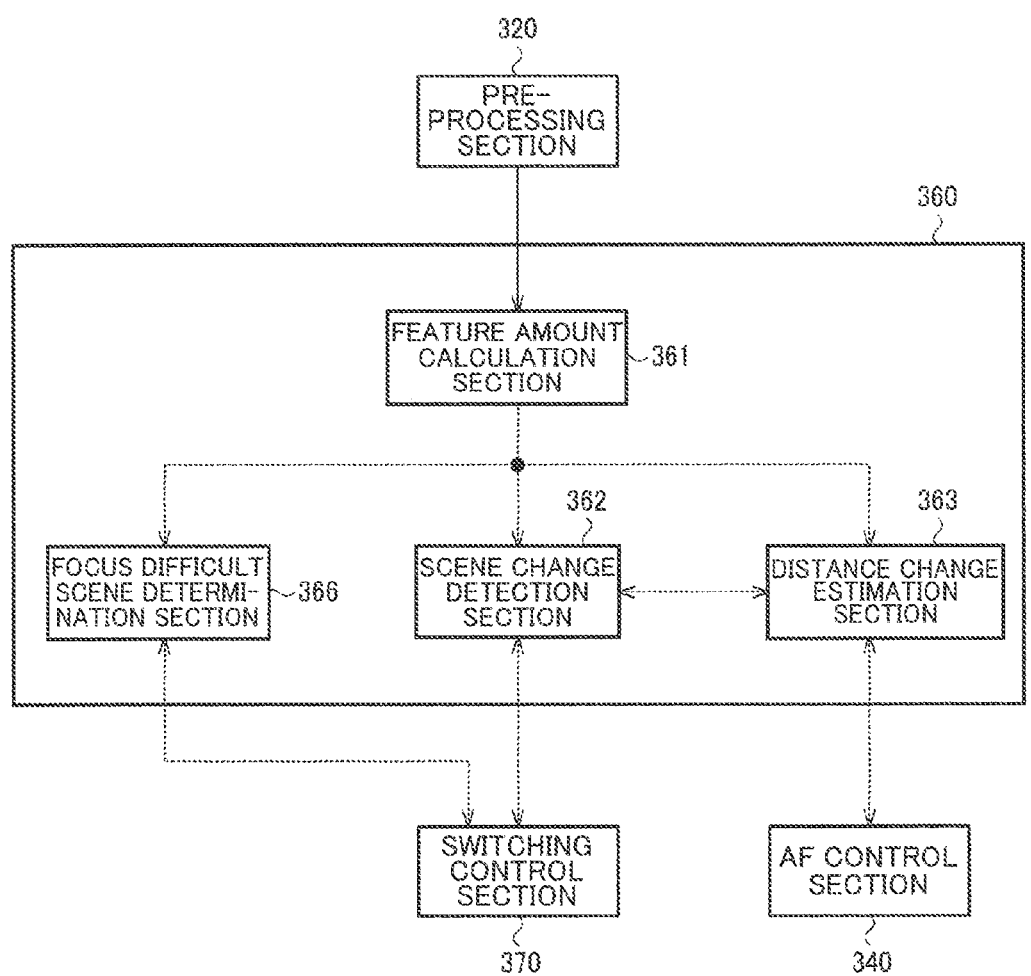
FIG. 9 illustrates a configuration example of a scene status determination section configured to perform focus difficult scene determination.

The scene status determination section 360 according to the second modification includes a focus difficult scene determination section 366 in addition to the configuration illustrated in FIG. 3, as illustrated in FIG. 9.

The focus difficult scene determination section 366 determines a focus difficult scene where the object is difficult to bring into focus with the AF control. The focus control section 315 (switching control section 370) performs the switching control to switch from the AF mode to the MF mode, when the focus difficult scene determination section 366 determines that the current scene is the focus difficult scene.

The focus difficult scene determination section 366 determines that the current scene is the focus difficult scene when the peak of the contrast value fails to be detected with the AF control, when the focus control cannot be completed for a predetermined period, or when the focus control cannot completed even when the AF control is performed for a predetermined number of times. The focus difficult scene determination section 366 that uses the contrast value for the determination acquires the feature amount including the contrast value from the feature amount calculation section 361.

Thus, the object can be brought into focus as the user intended, even when the object is difficult to bring into focus with the AF control.

For example, when the focus control mode is switched to the MF mode with the focus lens 220 moved to a position where the object is completely out of focus, the user needs to start the focusing operation from a process of finding a position where the object can be somewhat brought into focus. Thus, when the focus control mode is switched to the MF mode with the focus lens 220 moved to a position where the object is somewhat brought into focus, the user only needs to perform fine adjustment of the position of the focus lens 220.

Thus, the focus control section 315 (actuator control section 390) moves the focus lens 220 to a predetermined position, when the switching control is performed to switch from the AF mode to the MF mode, based on the determination result obtained by the focus difficult scene determination section 366.

The predetermined position may be a balanced position set in advance in such a manner that the object is likely to be somewhat brought into focus over a range between the near point and the far point, or may be set by the user at any appropriate position with the external I/F section 500 based on his or her preference.

Thus, the user can easily perform a focus adjustment operation with the MF control.

4.2. Detail of Process

Figure 10:
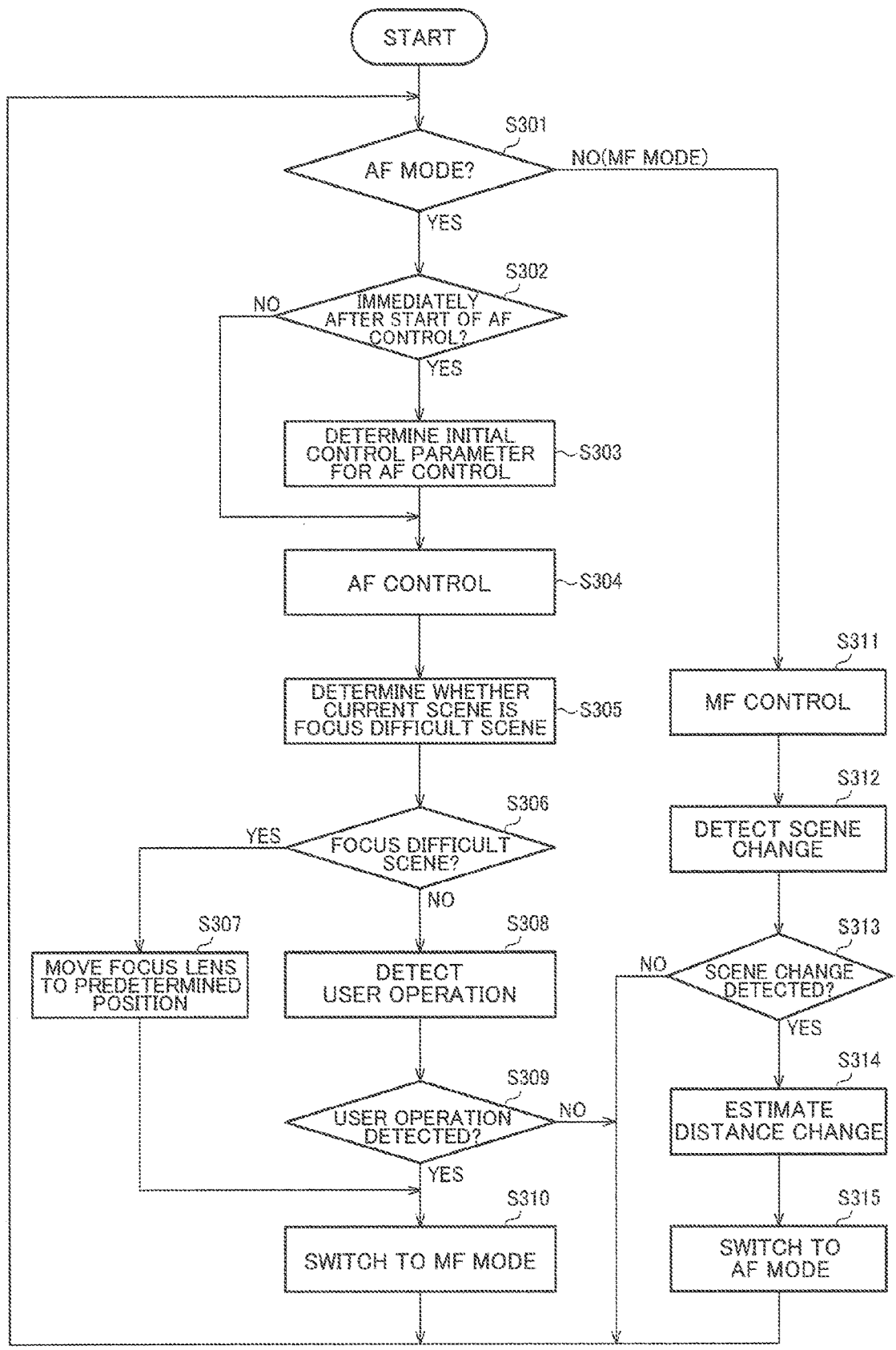
FIG. 10 is a flowchart illustrating a flow of a process according to a second modification.

Next, a flow of the process according to the second modification is illustrated in FIG. 10. A flow of the process in step S301 to step S304 and in step S311 to step S315 in FIG. 10 is the same as that of the process in step S101 to step S104 and step S108 to step S112 in FIG. 5 described above, and the description thereof is omitted.

In the second modification, as illustrated in FIG. 10, the focus difficult scene determination section 366 performs the focus difficult scene determination process after step S304 (S305). When the focus difficult scene determination section 366 determines that the current scene is the focus difficult scene (S306), the actuator control section 390 moves the focus lens 220 to the predetermined position (S307). Then, the switching control section 370 switches the focus control mode from the AF mode to the MF mode (S310), and the process returns to step S301. The order of steps S307 and S310 may be reversed.

When the focus difficult scene determination section 366 determines that the current scene is not the focus difficult scene (S306), the switching control section 370 detects information indicating whether or not the user has operated the focus lens operation section 210 (S308). When it is determined that the user operation has been detected (S309), the switching control section 370 switches the focus control mode from the AF mode to the MF mode (S310), and the process returns to step S301. When it is determined that the user operation has not been detected (S309), the process directly returns to step S301.

5. Third Modification

The first modification and the second modification described above may be combined.

For example, in a configuration where the scene change is detected based on the feature amount of the image, the scene status determination section 360 according to the present embodiment includes the feature amount calculation section 361, the scene change detection section 362, the distance change estimation section 363, the stable scene determination section 365, and the focus difficult scene determination section 366. The scene change detection section 362, the distance change estimation section 363, the stable scene determination section 365, and the focus difficult scene determination section 366 perform various processes based on the feature amount of the image obtained by the feature amount calculation section 361.

In a configuration where the scene change is detected based on the movement of the image capturing section 200, the scene status determination section 360 includes the feature amount calculation section 361, the scene change detection section 362, the distance change estimation section 363, the movement calculation section 364, the stable scene determination section 365, and the focus difficult scene determination section 366. In this configuration, the scene change detection section 362 detects a scene change based on the movement amount of the image capturing section 200 obtained by the movement calculation section 364. The distance change estimation section 363 estimates the distance change between the object and the image capturing section 200, based on the movement amount of the image capturing section 200 used by the scene change detection section 362. The stable scene determination section 365 and the focus difficult scene determination section 366 perform various processes based on the feature amount of the image obtained by the feature amount calculation section 361.

Figure 11:
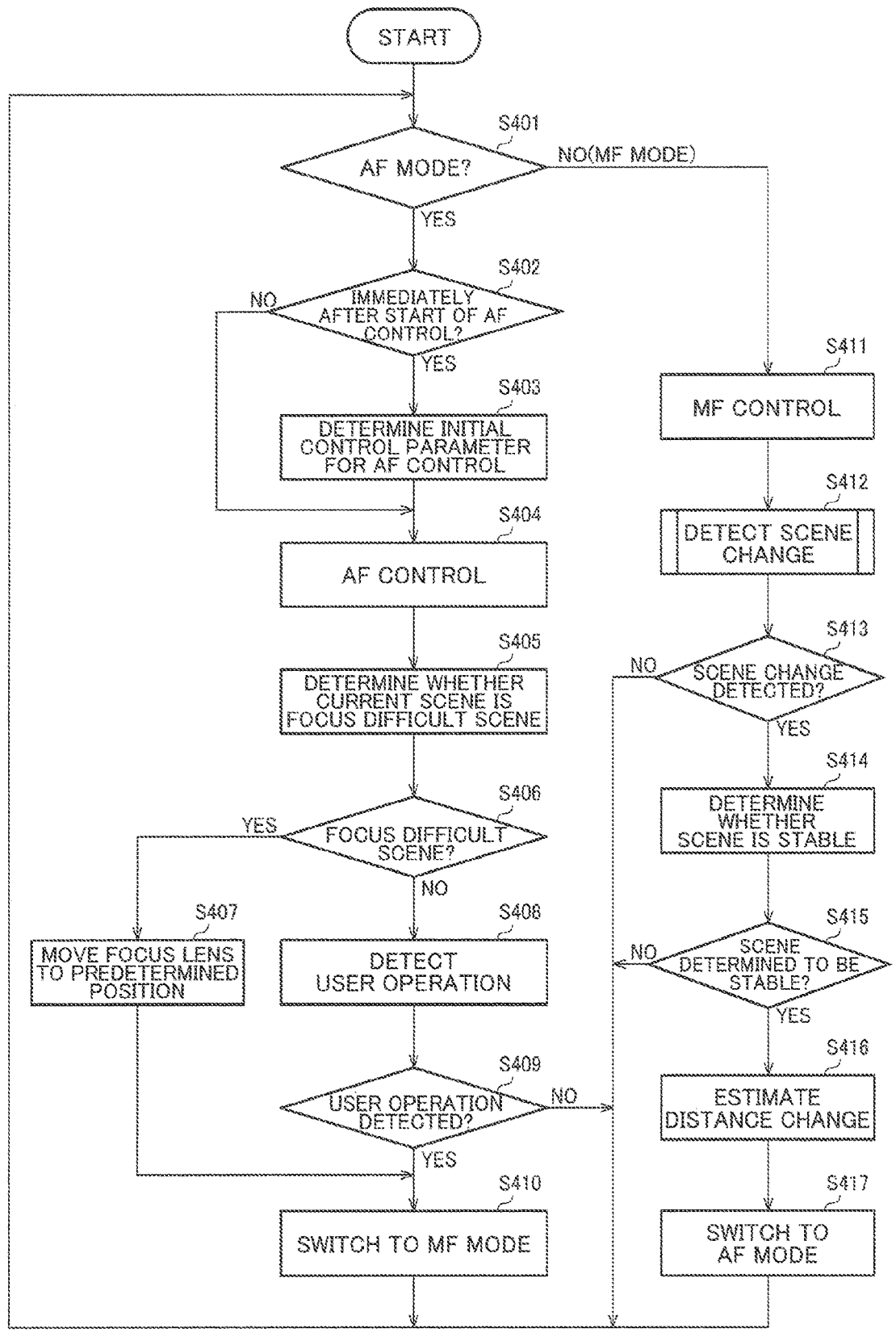
FIG. 11 is a flowchart illustrating a flow of a process according to a third modification.

FIG. 11 illustrates a flow of a process according to a third modification. A flow of the process in step S401 to step S410 in FIG. 11 is the same as that of the process in step S301 to step S310 in FIG. 10 described above. A flow of the process in step S411 to step S417 in FIG. 11 is the same as that of the process in step S208 to step S214 in FIG. 8 described above.

6. Fourth Modification

For example, once an object is brought into focus as the user intended during the surgery using the endoscope apparatus, this state is preferably maintained. This is because sudden switching between the MF mode and the AF mode might result in temporally blurring of the image displayed on the display section 400.

Thus, the image capturing device or the endoscope apparatus according to the present embodiment includes a lock operation section 260 that receives a lock operation by the user. The focus control section 315 disables the switching control process for switching between the MF mode and the AF mode when the lock operation is received by the lock operation section 260.

Thus, sudden switching between the MF mode and the AF mode, unintended by the user, can be prevented.

In a state where the lock operation is performed so that the switching control process for switching between the MF mode and the AF mode is disabled, the lock operation section 260 can receive an unlock operation by the user. The focus control section 315 starts the switching control process between the MF mode and the AF mode when the lock operation section 260 receives the unlock operation.

Thus, the user can enable the switching control process for switching between the MF mode and the AF mode, when the switching between the MF mode and the AF mode is required.

FIG. 12A to FIG. 12D illustrate specific examples of the lock operation section 260.

Figure 12A:
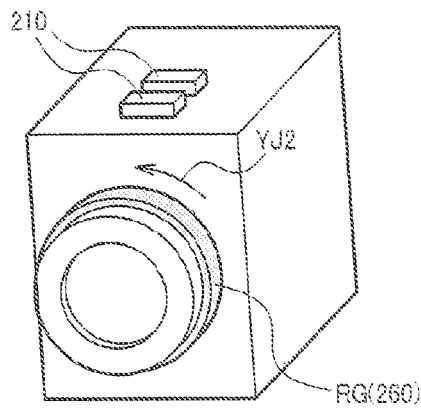
FIG. 12A to FIG. 12D illustrate a lock operation section.
Figure 12B:
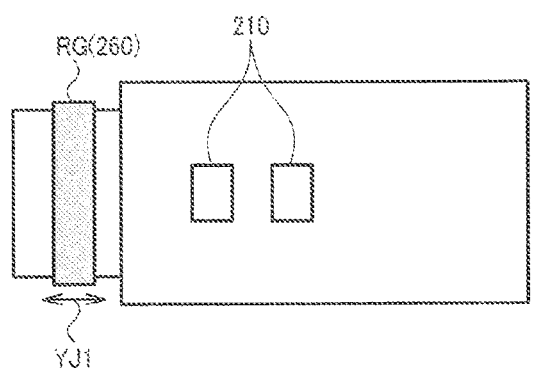

FIG. 12A and FIG. 12B are respectively a perspective view and a side view illustrating an example where a ring RG provided on the outer side of a barrel of the image capturing section 200 serves as the lock operation section 260. In the example illustrated in FIG. 12A and FIG. 12B, the switching control process for switching the focus control mode can be enabled and disabled with the ring RG slid in a thrust direction YJ1 (optical axis direction) and rotated in a radial direction YJ2 (direction orthogonal to the optical axis).

The lock operation section 260 and the focus lens operation section 210, illustrated as separate members in FIG. 12A and FIG. 12B, may be integrally formed. In such a configuration, the ring RG serves as the lock operation section 260 and the focus lens operation section 210, the switching control process for the focus control mode is enabled or disabled with the ring RG slid in the thrust direction and the movement of the focus lens 220 can be controlled with the ring RG rotated in the radial direction.

Figure 12C:
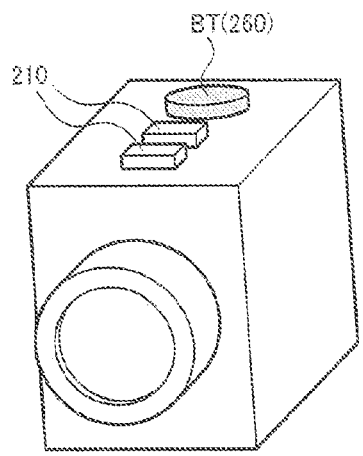
Figure 12D:
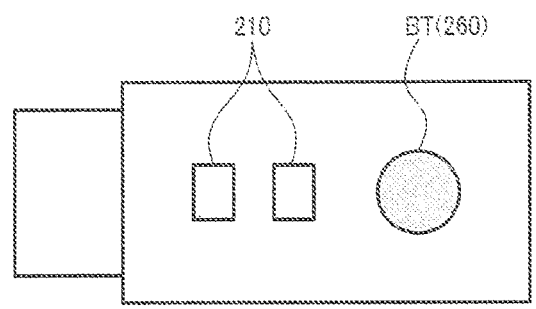

FIG. 12C and FIG. 12D are respectively a perspective view and a side view illustrating a configuration where a button BT serves as the lock operation section 260. In this configuration, the user can enable and disable the switching control process for the focus control mode by pressing the button BT. Note that a switch, a lever, or the like may be used as the lock operation section 260 instead of the button BT, and the switching control process for the focus control mode may be enabled or disabled by pressing a button corresponding to the focus lens operation section 210 for some amount of time. Thus, various modifications may be made.

7. Fifth modification

The image capturing device or the endoscope apparatus according to the present embodiment further includes a mode notification section 270 that notifies the user of one of the MF mode and the AF mode serving as the current set mode.

Figure 13B:
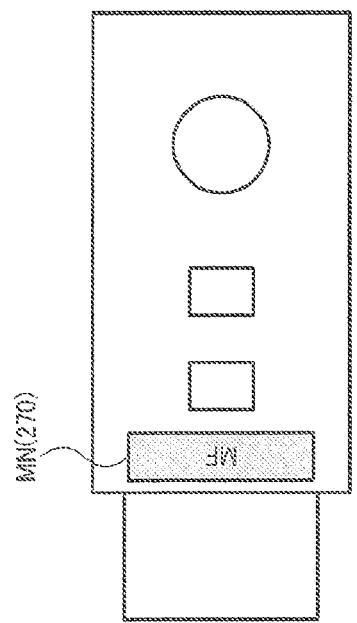
FIG. 13A to FIG. 13C illustrate a mode display section.
Figure 13C:
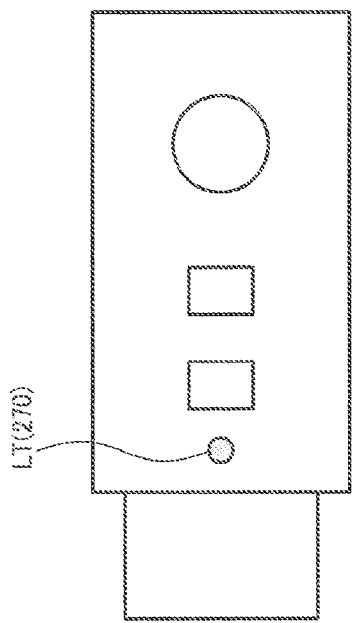
Figure 13A:
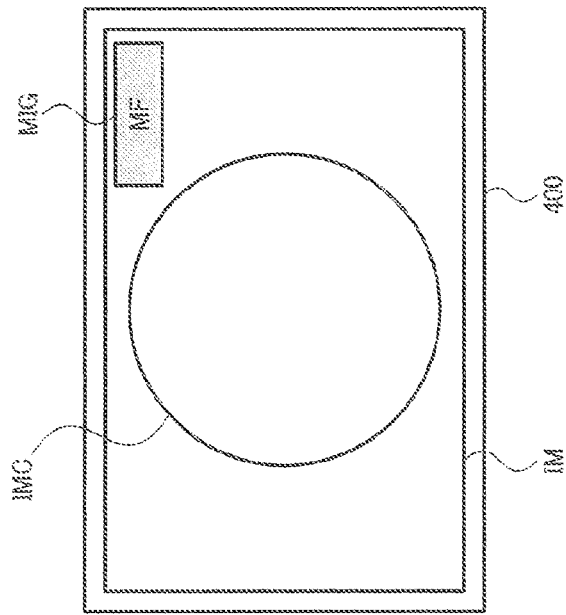

The mode notification section 270 is a mode display section illustrated in FIG. 13A to FIG. 13C for example.

FIG. 13A illustrates an example where a monitor (display section) 400 displays a captured image IM and an image MIG indicating the currently set mode on a part of the monitor 400. The image MIG is displayed on the outer side of the image circle IMC of the displayed image IM. In the example illustrated in FIG. 13, the image MIG indicates that the MF mode is currently set. In the example illustrated in FIG. 13A, the monitor 400 serves as the mode notification section 270.

FIG. 13B illustrates an example where a monitor MN is provided on the barrel of the image capturing section 200, and an image indicating the current mode is displayed on a part of the monitor MN. In the example illustrated in FIG. 13B, the monitor MN serves as the mode notification section 270.

FIG. 13C illustrates an example where a lamp LT is provided on the barrel of the image capturing section 200, and the currently set mode can be recognized based on whether or not the lamp is lit. Although not elaborated in the figure, a lamp that is ON when the AF mode is set and a lamp that is ON when the MF mode is set may be may be provided to the image capturing section 200, and the currently set mode may be recognized based on which one of the lamps is ON. In the example illustrated in FIG. 13C, the lamp LT serves as the mode notification section 270. The examples illustrated in FIG. 13A to FIG. 13C may be combined, and the mode notification section 270 may be modified in various ways. The mode notification section 270 is not limited to the mode display section and may notify the currently set mode with sound, vibration, or the like.

Thus, the user can check the currently set mode.

When the image capturing device or the endoscope apparatus includes the lock operation section 260 as in the fourth modification described above, the image capturing device or the endoscope apparatus according to the present embodiment may further include a lock status notification section (not illustrated) that displays a lock status for the switching control process for switching the focus control mode. For example, the lock status notification section a lock status display section. The lock status display section may be a monitor, a lamp, or the like also serving as the mode display section described above.

The processes of the image capturing apparatus, the endoscope apparatus, or the like according to the present embodiment may be partially or mainly implemented with a program. In such a configuration, the image capturing apparatus, the endoscope apparatus, or the like according to the present embodiment is implemented when a processor such as a CPU executes the program. Specifically, a program stored in a non-transitory information storage device is read out and is executed by the processor such as a CPU. The information storage device (computer-readable device) stores a program and data, and has functions that can be implemented by an optical disk (e.g., CD-ROM and DVD), a hard disk drive (HDD), or a memory (e.g., memory card and ROM). The processor such as a CPU performs various processes according to the present embodiment based on a program (data) stored in the information storage device. Thus, the information storage device stores a program for causing a computer (a device including an operation section, a processing section, a storage section, and an output section) to function as each section according to the present embodiment (program for causing the computer to execute processes of each section).

Although only some embodiments of the present invention and the modifications thereof have been described in detail above, those skilled in the art will readily appreciate that many modifications are possible in the embodiments without materially departing from the novel teachings and advantages of the invention. Accordingly, all such modifications are intended to be included within scope of the invention. For example, any term cited with a different term having a broader meaning or the same meaning at least once in the specification and the drawings can be replaced by the different term in any place in the specification and the drawings. The configurations and the operations of the image capturing apparatus and the endoscope apparatus are not limited to those described above in connection with the embodiments. Various modifications and variations may be made of those described above in connection with the embodiments.

What is claimed is:

1. An image capturing device comprising:
a processor including hardware, the processor being configured to implement:
a switching control process for switching between a manual focus mode of performing manual focus control and an auto focus mode of performing auto focus control;
a process for controlling driving of a focus lens of an image capturing section;
a scene status determination process for performing a detection process for detecting a scene change during the manual focus mode and an estimation process for estimating distance change information indicating distance change between the image capturing section and an object;
controlling the driving of the focus lens based on lens drive information input by a user through a focus lens operation section in the manual focus mode;
switching control for switching from the manual focus mode to the auto focus mode when the scene change is detected by the scene status determination process;
determining a control scheme for the auto focus control as an initial control parameter at a start of the auto focus control based on the distance change information estimated by the scene status determination process in the manual focus mode; and
controlling the driving of the focus lens to bring the object into focus based on a parameter different from the distance change information in accordance with the determined control scheme in the auto focus mode.

2. The image capturing device as defined in claim 1, the processor estimating, when the scene change is detected, the distance change information indicating the distance change in a scene change detection period that is a predetermined period until the scene change is detected.

3. The image capturing device as defined in claim 2, the processor determining a target movement direction of the focus lens as at least one parameter serving as the initial control parameter, based on the distance change information.

4. The image capturing device as defined in claim 2,
the processor determining a target movement amount of the focus lens as at least one parameter serving as the initial control parameter, based on the distance change information.

5. The image capturing device as defined in claim 2,
the processor determining a target position of the focus lens as at least one parameter serving as the initial control parameter, based on the distance change information.

6. The image capturing device as defined in claim 2,
the processor determining a control scheme for the auto focus control as at least one parameter serving as the initial control parameter, based on the distance change information.

7. The image capturing device as defined in claim 1,
the processor performing stable scene determination for determining whether or not a scene of image capturing by the image capturing section is stable; and
the auto focus control when the scene is determined to be stable by the stable scene determination.

8. The image capturing device as defined in claim 7,
the processor determining whether or not the scene is stable after scene change has been detected by the scene status determination process.

9. The image capturing device as defined in claim 1,
the processor performing a process of receiving a lock operation by the user; and
disabling the switching control process for switch between the manual focus mode and the auto focus mode, when the lock operation is received.

10. The image capturing device as defined in claim 1,
the processor performing the estimation process for the distance change information based on information obtained by the detection process for the scene change.

11. The image capturing device as defined in claim 1,
the processor performing the detection process for the scene change and the estimation process for the distance change information based on a change amount of a feature amount of a captured image captured by the image capturing section.

12. The image capturing device as defined in claim 11,
the processor determining that the scene change has occurred when the change amount of the feature amount of the captured image continuously exceeds a given threshold for a given period of time of more.

13. The image capturing device as defined in claim 1,
the processor performing the detection process for the scene change and the estimation process for the distance change information based on a movement of the image capturing section.

14. The image capturing device as defined in claim 13,
the processor determining that the scene change has occurred when an amount of the distance change indicated by the distance change information estimated continuously exceeds a given threshold for a given period of time or more.

15. The image capturing device as defined in claim 13,
the processor determining that the scene change has occurred when an integrated value of an amount of the distance change indicated by the distance change information estimated is determined to have exceeded a given threshold.

16. The image capturing device as defined in claim 1,
the processor performing focus difficult scene determination to determine whether or not a current scene is a focus difficult scene where the object is difficult to bring into focus with the auto focus control; and
the switching control for switching from the auto focus mode to the manual focus mode when the current scene is determined as the focus difficult scene by the focus difficult scene determination.

17. The image capturing device as defined in claim 16,
the processor moving the focus lens to a predetermined position when the switching control to switch from the auto focus mode to the manual focus mode has been performed based on a determination result of the focus difficult scene determination.

18. The image capturing device as defined in claim 1,
the processor performing a mode reporting process to report the manual focus mode or the auto focus mode as a currently set mode.

19. An endoscope apparatus comprising the image capturing device as defined in claim 1.

20. A method for operating an image capturing device, the method comprising:
performing a switching control process for switching between a manual focus mode of performing manual focus control and an auto focus mode of performing auto focus control;
performing a process for controlling driving of a focus lens of an image capturing section;
performing a detection process for detecting a scene change during the manual focus mode;
performing an estimation process for estimating distance change information indicating distance change between the image capturing section and an object;
controlling the driving of the focus lens based on lens drive information input by a user through a focus lens operation section in the manual focus mode;
performing switching control for switching from the manual focus mode to the auto focus mode when the scene change is detected;
determining a control scheme for the auto focus control as an initial control parameter at a start of the auto focus control based on the distance change information estimated by the estimation process in the manual focus mode; and
controlling the driving of the focus lens to bring the object into focus based on a parameter different from the distance change information in accordance with the determined control scheme in the auto focus mode.

* * * * *